(12) United States Patent
Hodosh

(10) Patent No.: US 7,115,252 B2
(45) Date of Patent: Oct. 3, 2006

(54) THERAPEUTIC COMPOSITIONS AND METHODS OF USE THEREOF

(76) Inventor: Milton Hodosh, 2 Harian Dr., Providence, RI (US) 02906

( * ) Notice: Subject to any disclaimer, the term of this patent is extended or adjusted under 35 U.S.C. 154(b) by 19 days.

(21) Appl. No.: 10/144,235

(22) Filed: May 13, 2002

(65) Prior Publication Data

US 2003/0003163 A1    Jan. 2, 2003

Related U.S. Application Data

(63) Continuation-in-part of application No. PCT/US00/31086, filed on Nov. 13, 2000, which is a continuation-in-part of application No. 09/633,424, filed on Aug. 7, 2000, now Pat. No. 6,524,623, which is a continuation-in-part of application No. 09/439,858, filed on Nov. 12, 1999, now Pat. No. 6,099,868.

(51) Int. Cl.
    *A61K 8/18*      (2006.01)
    *A61K 31/34*    (2006.01)
    *A61K 33/00*    (2006.01)
    *A61K 33/14*    (2006.01)
    *A61K 33/42*    (2006.01)

(52) U.S. Cl. ................ 424/49; 514/470; 424/601; 424/610; 424/662; 424/673; 424/718

(58) Field of Classification Search .......... 424/49, 424/601, 610, 662, 673, 718; 514/470
See application file for complete search history.

(56) References Cited

U.S. PATENT DOCUMENTS

| | | |
|---|---|---|
| 3,863,006 A | 1/1975 | Hodosh |
| 4,060,600 A | 11/1977 | Vit |
| 4,191,750 A | 3/1980 | Hodosh |
| 4,343,608 A | 8/1982 | Hodosh |
| 4,400,373 A | 8/1983 | Hodosh |
| 4,407,675 A | 10/1983 | Hodosh |
| 4,525,343 A | 6/1985 | Raaf |
| 4,585,649 A | 4/1986 | Lynch |
| 4,610,871 A | 9/1986 | Lynch |
| 4,610,872 A | 9/1986 | Lynch |
| 4,627,974 A | 12/1986 | Lynch |
| 4,627,975 A | 12/1986 | Lynch |
| 4,627,976 A | 12/1986 | Lynch |
| 4,627,978 A | 12/1986 | Lynch |
| 4,627,979 A | 12/1986 | Lynch |
| 4,627,980 A | 12/1986 | Lynch |
| 4,632,937 A | 12/1986 | Lynch |
| 4,711,904 A | 12/1987 | Luzzi et al. |
| 4,770,871 A | 9/1988 | Greenshields |
| 4,866,048 A | 9/1989 | Calverley et al. |
| 4,961,923 A | 10/1990 | Heyde |
| 5,015,466 A | 5/1991 | Parran, Jr. et al. |
| 5,032,388 A | 7/1991 | Tikkanen |
| 5,120,460 A | 6/1992 | Asai et al. |
| 5,139,768 A | 8/1992 | Friedman |
| 5,147,632 A | 9/1992 | Pan et al. |
| 5,153,006 A | 10/1992 | Hodosh |
| 5,374,417 A | 12/1994 | Norfleet et al. |
| 5,403,577 A | 4/1995 | Friedman |
| 5,522,726 A | 6/1996 | Hodosh |
| 5,875,798 A * | 3/1999 | Petrus ................ 132/321 |
| 6,099,868 A | 8/2000 | Hodosh |
| 6,524,623 B1 * | 2/2003 | Hodosh ............... 424/600 |

OTHER PUBLICATIONS

Medline Abstract, Brayer et al., Refu'at ha-peh veha-shinayim (Tel Aviv, Israel : 1969), (Oct. 1977), 26(4), 45-7.*
Martindale, The Extra Pharmacopoeia, 28th ed., Reynolds et al. (eds.), published 1982 by The Pharmaceutical Press (London) pp. 1746-1747.*
Killoy, "Local Delivery of Antimicrobials: A New Era in the Treatment of Adult Periodontitis", Compendium of Continuing Education in Dentistry (Jamesburg, N.J.:1995), (1999) 20 (4 suppl) 13-8; quiz 34-5.*
Westfelt, "Rationale of Mechanical Plaque Control", J. Clin. Periodontol., 1996; 23: 263-267.*
Merz et al., The Secondary Prevention of Coronary Artery Disease, Jun. 1997, The American Journal of Medicine, vol. 102, pp. 572-581.*
Medline Abstract, Accession No. 2002176326, Killoy, Compendium of Continuing Education in Dentistry (Jamesburg, N.J.:1995), (1999) 20 (4 suppl) 13-8; quiz 34-5.*
Remington's Pharmaceutical Sciences, 16th edition, 1980, pp. 216-218.*
Alfred N. Martin et al., Physical Pharmacy, 2nd edition, published 1969 by Lea & Febiger (PA), pp. 175-176.

* cited by examiner

*Primary Examiner*—Raymond J. Henley, III
(74) *Attorney, Agent, or Firm*—Salter & Michaelson

(57) ABSTRACT

A method and composition for the restoration and maintenance of gingival and periodontal health are provided. The composition includes a potassium as an essential ingredient, which acts as an anti-bacterial agent. In some embodiments, the compositions include an osmotic agent other than potassium.

44 Claims, No Drawings

THERAPEUTIC COMPOSITIONS AND METHODS OF USE THEREOF

CROSS REFERENCE TO RELATED APPLICATIONS

This application is a continuation-in-part under 35 U.S.C. § 120 to commonly owned PCT application Ser. No. PCT/US00/31086, filed on Nov. 13, 2000, which is a continuation-in-part of commonly owned U.S. application Ser. No. 09/633,424, filed Aug. 7, 2000, now U.S. Pat. No. 6,524,623, which is a continuation-in-part of commonly owned U.S. Pat. No. 6,099,868, based on Ser. No. 09/439,858 filed on Nov. 12, 1999, each of which is incorporated herein by reference in its entirety.

BACKGROUND

1. Technical Field

The present application is directed to a composition and method for preventing the formation of plaque and, in particular, to a composition that includes potassium as an antibacterial or an osmotic agent.

2. Related Art

Dental plaque consists of bacterial deposits firmly adhered to teeth. Plaque is neither food or food residue, nor is it just some form of bacteria from the mouth. It is a complex metabolically interconnected, highly organized bacterial system. It consists of dense masses of a large variety of microorganisms embedded in an intermicrobial matrix. In sufficient concentration and with metabolic development, it may disturb the balance of the host-parasite relationship and thereby cause problems such as caries, gingival disease, periodontal disease, and the like. The total counts of microorganisms in dental plaque from the gingival sulcus area have shown the presence of $10^8$ microorganisms/milligram. The intermicrobial matrix is present in only small amounts compared to the large number of microorganisms present. The gingival region of a person with periodontal disease may harbor 200 mgs. of plaque microbiota. This provides an astronomical number of microorganisms that are in contact with gingival tissues. With metabolic development, it can disturb the balance of the host-parasite relationship and thereby cause dental caries, periodontal disease, and mouth odor.

Dental calculus is dental plaque that has undergone mineralization. Bacterial plaque, and calculus continue to form alternatively in layers. Certain oral bacteria are shown to stick to tooth surfaces and to each other by means of extracellular polysaccharides. Both glycans (dextran polysaccharides) and fructans (levans) are synthesized extracellularly by certain bacteria, using sucrose as a substrate. These polysaccharides play an important role in plaque dynamics.

Chronic marginal gingivitis is the most common gingival disease. It is seen in response to the putative bacteria (Acetometacomitans, Gingivales, Bacteroides and others) that are attached to tooth surfaces. The disease may remain stationary for an indefinite period of time, or it may go on to infect and injure the deeper periodontal structures. Gingival disease may be conditioned by systemic factors such as diabetes, hyperthyroidism, pregnancy, puberty, vitamin C deficiency, and it may respond to pathologic agents by gingival enlargement.

Periodontal disease is a destructive inflammatory condition initiated by bacterial plaque accumulation in the gingivo-dental anatomy. "Gingivo-dental anatomy," as used herein, means the gums and teeth of a subject. It is initially confined to the gingivae, and as it progresses in severity it spreads to involve the deeper periodontal tissues. Inflammation is present in all forms of gingival disease because bacterial plaque, which causes the inflammation, along with local irritational factors that favor plaque accumulation, are present within the gingival enlargement. Plaque induced inflammation gives rise to degenerative, necrotic, and proliferative gingival changes. Atrophy, hyperplasia, and neoplasm can occur in the gingivii.

Pathologic changes accompanying gingivitis are associated with the presence of oral micro-organisms in the gingival sulcus. These organisms synthesize harmful emissions that are capable of causing cellular damage to epithelial and connective tissue cells, collagen, proteoglycans, and glycocalyx (cellular glycoprotein and polysaccharide coat). Widening of the intercellular spaces between junctional epithelial cells in early gingivitis creates a pathway for injurious emissions released by the bacteria to access the connective tissue and penetrate it to sufficiently spread the disease to the deeper tissues.

The first stage of gingival inflammation is vascular dilatation of capillaries which brings forth increased blood flow. Next, gingival erythema may appear due to proliferation of capillary loops between rete pegs. Newly experienced bleeding with probing is an early sign of gingivitis.

In the second stage of chronic gingivitis blood vessels became engorged, and congested, with slow venous return making blood flow sluggish. This results in localized pooling of blood and gingival anoxemia which imparts a bluish hue upon the reddened gingivae. Extravasation of the red blood cells into the connective tissues along with hemoglobin breakdown into the various pigments of bilirubin and hematoidin also deepens the color of chronically inflamed gingivae. Chronic inflammatory gingivae alters the epithelial/connective tissue relationship, pocketing ensues, and color changes are clinically observed. The epithelium proliferates, and rete pegs lengthen downward into the connective tissue. At the same time, the increasing gingival mass of the inflamed connective tissues presses against the overlying epithelium causing it to thin. The engorged blood vessels of the connective tissue extend into the surface epithelium cells, accentuating redness.

With chronic gingivitis and chronic destructive periodontal disease, tissue destruction and tissue repair occur simultaneously. The nature and vitality of the bacteria and the presence or absence of local irritants as related to the strength of one's immune system determine the course of the disease. Persistent local irritants injure the gingivae, prolong inflammation, and cause vascular permeability and exudation. New epithelial and connective tissue cells, collagen fibers, proteoglycans, and blood vessels form even as destructive breakdown affects the gingival color, contour, consistency, size, and surface texture. When increased vascularity, exudation, and tissue degeneration predominate there are marked color changes. On occasion Fibrosis is the main feature with chronic inflammation. In this circumstance the gingivae will have a more normal color.

The putative bacteria that cause periodontal disease are contained in the plaque on the teeth facing the gingival sulci. Their emissions penetrate the periodontal pockets, gingivae, and connective tissues. In addition to direct initiation of the inflammatory response by microbial irritants, periodontal inflammation may be produced indirectly by immunopathologic processes set in action by penetration of microbial antigens into the tissues.

If the periodontal tissue destructive factors are able to outpace the rate of tissue repair, then inflammation exacerbates along with permeability and penetration of the bacterial toxic emissions. The production of new epithelial and connective tissue cells, collagen, proteglycans, along with new blood vessel formation are unable to keep pace with tissue destruction and degeneration of the periodontium. Damage to epithelial and connective tissue cells, collagen, proteoglycans, cellular glycoprotein and polysaccharide coat will ensue, and the disease spreads to the deeper tissues leading to ever more deterioration.

The patent literature is replete with examples of attempts to address problems resulting from plaque and calculus formation. One attempt is disclosed in U.S. Pat. No. 4,585,649 to Lynch dated Apr. 29, 1986, which discloses that various compositions containing monoalkyl and dialkyl ethers of dianhydrohexitols as an essential ingredient are effective in the treatment of oral surfaces and cavities to reduce irritation and plaque accumulation caused by the action of S. Mutans. The compositions of Lynch require 5–95%, by weight, of the dianhydrohexitols. Lynch discloses that the population of S. mutans is drastically reduced in the environment of the dianhydrohexitol derivatives.

Recently, the presence of gum disease amplified by its inflammatory response has been linked to coronary thrombosis. The inflammatory response and the associated high C-reactive protein (CRP) levels released by the liver in human serum provides reason to suspect a higher occurrence of CAD (cardiac arterial disease) among people with periodontal disease when compared with those free-of periodontal disease. Some data confirms that patients suffering from CAD are more likely to have periodontal disease than a comparable population without periodontal disease. Thus, prevention and treatment of periodontal disease may well become a strategy for prevention among patients with risk of coronary artery disease or as a means of secondary prevention for those surviving an acute myocardial infection (AMI).

Inflammation is becoming increasingly recognized for its important role among patients presenting with acute coronary syndromes. High CRP (HsCRP) blood levels and an increasing WBC (white blood count) appear to be a significant predictor of death in myocardial infarctions.

In the opinion of some researchers, infection and inflammation also contributes to atherosclerotic disease.

DETAILED DESCRIPTION OF THE PREFERRED EMBODIMENTS

The present disclosure is based on the discovery that potassium is effective as an antibacterial agent and that the antibacterial effectiveness of potassium may be substantially improved when used in compositions containing an osmotic agent. When contained in compositions intended for oral use, potassium may be effective for preventing the formation of plaque and calculus. The compositions also may be effective for treating and/or reversing damage caused by plaque or calculus formation, including gingival and/or periodontal disease. Thus, the compositions and methods of the present disclosure facilitate the achievement of a dentition effectively free of microbial plaque.

The compositions and methods may be effective for preventing caries by effectively destroying caries producing bacteria (e.g. streptococcus viridans). The compositions and methods also may be effective for treating and/or preventing chronic diseases such as chronic gingivitis and chronic destructive periodontal disease, by preventing tissue destruction. The compositions and methods also may be effective for repairing tissue that has been destroyed as a result of the same diseases.

Although not wishing to be bound by any theory, it is hypothesized that the present compositions draw water from the invading bacteria that are responsible for causing plaque formation. This mechanism is thought to be similar to that disclosed in commonly owned and co-pending U.S. patent application Ser. No. 09/633,424, filed on Aug. 7, 2000. Bacteria have a resting membrane potential, the same as do nerves, and also may be depolarized and caused to shrink in volume. Bacterial cells so shrunken are unable to reproduce and function normally. They become inert, less viable, and non-virulent.

After depolarization and reduction in volume, a secondary effect of the present compositions is that they are thought to enter the invading bacterial cells, along with water, tearing apart the cell's membrane (lysis). As the compositions enter the bacterial cells, the bacterial cell membranes are caused to increase in volume, causing the membrane to lyse. When this happens, all bacterial enzymes, substrates, nutrients, and other vital fluids are lost to the saliva. At this point the bacteria are essentially dead, and their endotoxins and enzyme emissions no longer are synergized and released into the periodontium.

The bacteria lose their potency when they are caused to depolarize, shrink in size, then swell causing their membranes to lyse. Bacterial plaque responsible for causing periodontal disease and caries are thus inactivated, and destroyed. Thus, their ability to damage periodontal tissues and to cause periodontal inflammation is substantially impaired and/or eliminated. By impairing and/or eliminating the destructive capacity of the bacteria, the tissues' reparative phase may proceed unopposed by potent, constantly multiplying bacteria. As a result, the gingivii may improve toward normalcy. The gingivii under these conditions has been found to be amazingly resilient having a strong capability to heal once the bacteria and their emissions, and the gingival inflammation have been eliminated.

The physical flow of saliva and teeth brushing acts to remove food, cellular debris, and destroyed bacteria (and bacterial debris) for elimination via the alimentary tract. The rate of salivary clearance can be a deterrent against renewed plaque formation and along with the use of the present compositions, reduce the caries incidence, inflammatory gingival disease, and mouth odor.

In one embodiment, the present disclosure is directed to a composition that contains an effective amount of potassium, from a non-toxic potassium containing compound, as an active ingredient or active agent. In some embodiments, the compositions contain an effective amount of potassium, from a non-toxic potassium containing compound, as an essential active ingredient.

Potassium containing compounds suitable for the present compositions include, but are not limited to, potassium bicarbonate, potassium biphthalate, potassium bromide, potassium chromate, potassium acetate, potassium dichromate, potassium phosphate, potassium sulfate, potassium chromium sulfate, potassium citrate, potassium thiocyanate, potassium alum, potassium bitartrate, potassium bromate, potassium carbonate, potassium chlorate, potassium chloroglatinate, potassium chloride, potassium hydroxide, potassium perchlorate, potassium persulfate, potassium oxalate, potassium azide, potassium fluoride, potassium hydrogen sulfate, potassium iodate, potassium sodium tartrate, potassium fluoride, tartrate, and combinations thereof.

Particularly preferred potassium containing compounds include potassium chloride, potassium fluoride, and potassium nitrate.

The present compositions preferably contain at least about 0.5 percent, more preferably at least about 10 percent, more preferably at least about 20 percent of the potassium containing compounds. In particularly preferred embodiments, the compositions of the present disclosure may be saturated with a potassium containing compound. "Saturated," as used herein, means that the composition contains the maximum equilibrium quantity of the potassium containing compound at ambient conditions. Of course, the amount of potassium containing compound required to saturate the compositions will vary according to the formulation of the composition and the solubility of the selected potassium containing compound in the formulation. For example, when potassium nitrate is used in a water-based composition, typical concentrations of the potassium nitrate are about 35%, by weight.

In another embodiment, the compositions also may include an osmotic agent. "Osmotic agent," as used herein, means any agent that raises the osmotic pressure of fluid on one side of a membranous structure drawing water across the membrane, causing the structure to shrink in volume. The osmotic agents enhance the activity of the active ingredients or active agents, as described in the foregoing related applications. Suitable osmotic agents include the monoalkyl and dialkyl ethers of dianhydrohexitols described in the foregoing Lynch patent, including methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof. Dimethyl isosorbide is particularly preferred in the present compositions due to its commercial availability. When included, the present compositions preferably contain about 1 percent to about 90 percent, more preferably about 15 percent to about 55 percent, and more preferably still from about 25 percent to about 45 percent, of at least one of the foregoing osmotic agents.

One preferred composition includes an effective amount both potassium nitrate and of dimethylisosorbide. Preferably, the present compositions contain from about 1 percent to about 90 percent of dimethylisosorbide, and from about 1 percent up to the saturation level of a potassium nitrate, with the remainder comprising water, and other ingredients such as flavorants.

Potassium from the potassium containing compounds may function as an osmotic agent in some instances, such as when the potassium containing compounds are contained in the compositions at or near saturation levels. At such saturation levels, it may not be necessary to include an osmotic agent in order to achieve the same results. That is, plaque formation may be prevented or treated using a composition saturated or nearly saturated with at least one of the foregoing potassium containing compounds.

The compositions described above are administered or applied in effective amounts. An effective amount is a dosage of the composition sufficient to provide a medically desirably result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, an effective amount for treating chronic periodontal disease would be an amount sufficient to slow or halt the development or further progression of gingival and periodontal disease, caries, or mouth odor (halitosis or fetor exor). It is preferred generally that a maximum dose be used, that is, the highest safe dose according to sound medical judgment.

It is expected that the compositions may be applied topically to the oral mucosa or skin in one or several administrations per day. In the event that a response in the subject is insufficient at the initial doses applied, higher doses (or effectively higher doses by a different, more localized delivery route) may be employed to the extent that patient tolerance permits. Multiple doses per day are contemplated to achieve appropriate absorption levels of compounds.

When administered, the compositions may be applied in pharmaceutically-acceptable amounts and in pharmaceutically-acceptably compositions delivered in mouth rinses, toothpastes, toothpaste/containing mouthrinses, confections, lozenges, chewing gum, gels applied topically, ointments applied topically or by prefabricated or custom-made trays. They can be delivered in unit dose preparations. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or, alkaline earth salts, such as sodium, potassium or calcium salts.

The compositions may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active agent is combined to facilitate the application. The components of the osmotic agents and the active agents also are capable of being co-mingled with such carriers, other additives, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal. The compositions may also include a variety of other materials such as solvents, surfactants, thickeners, colorants, flavorants, and the like.

A variety of administration routes are available. The particular mode selected will depend of course, upon the particular active agent selected, whether an osmotic agent is included, the severity of the condition being treated and the dosage required for therapeutic efficacy. The methods of the disclosure, generally speaking, may be practiced using any mode of administration that is medically acceptable, meaning any mode that produces effective levels of the active agents without causing clinically unacceptable adverse effects. According to one particular characteristic of the disclosure, these products are used for the preparation of a pharmaceutical composition intended for local topical or oral application, and may be in any suitable form including mouthwash, liquids, pastes, liquid/paste combinations, creams, ointments, gels, lotions, chewing gum, confection, adhesive pads, trays, or any other form that will dissolve in the mouth. The pharmaceutical composition may also be in the form of a liquid, soft capsules, solution, or transdermal patches to treat skin bacterial infection containing the active agent. The compositions may also be administered by providing the composition in, for example, a bleaching tray or embedded in a material for placement in proximity to the gingivo-dental anatomy. Such modes of administration include topical routes.

The pharmaceutical compositions may conveniently be presented in unit dosage form and may be prepared by any of the methods well known in the art of pharmacy. All methods may include the step of bringing the active agents and osmotic agents into association with a carrier which constitutes one or more accessory ingredients. In general, the compositions may be prepared by uniformly and intimately bringing the active agents into association with a liquid carrier, a finely divided solid carrier, or both, and then, if necessary, shaping the product.

Compositions suitable for oral administration may be presented as discrete units, such as capsules, dissolving or effervescent tablets, condiments, chewing gum, tablets, lozenges, each containing a predetermined amount of the active agents, osmotic agents, or both. Other compositions include suspensions in aqueous liquids or non-aqueous liquids such as a mouthwash, syrup, creams, elixir or an emulsion.

Other delivery systems can include time-release, delayed release or sustained release delivery systems. Such systems can avoid repeated administrations of the active agents described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like.

Use of a long-term sustained release implant may be particularly suitable for treatment of chronic conditions. Long-term release, are used herein, means that the implant is constructed and arranged to deliver therapeutic levels of the active agent for at least 30 days, and preferably 60 days. Long-term sustained release implants are well-known to those of ordinary skill in the art and include some of the release systems described above.

The present compositions facilitate a method of use that prevents periodontal disease in a subject and/or treats existing periodontal disease in a subject. The method involves using the foregoing compositions on a periodic basis for a period of time, preferably in a mouthwash or dentifrice. Preferably, the present compositions are used on a daily basis as part of a regular dental hygiene program. Preferably, the compositions may be used in a regular rinse regime b.i.d.
about the gingivo-dental anatomy for 1–2 minutes for 5 weeks followed by regular maintenance usage.

When used on a regular basis by a subject, favorable conditions may be created that allow the reparative phase of periodontal disease to work positively. When used in a regular regime, the present compositions may provide chemically induced bacterial plaque control. With regular usage the topically applied composition facilitates achievement of a dentition effectively free of destructive microbial plaque. It enhances the healing of chronic gingivitis and chronic destructive periodontal disease with and without bone loss, and ulcerative lesions such as aphthous stomatitis, herpes, aids induced, and radiation, post-radiation, and chemotherapeutic induced ulcers (mucositis) may be cured more rapidly and pain may be markedly reduced and/or eliminated.

When used in conjunction with conventional treatment procedures for the treatment of advanced periodontal conditions (bone grafts, soft tissue grafts, guided tissue regeneration, gingivoplasty, etc.) it may enhance the gingival recovery process, and provide rapid and improved healing, with notably less post surgical pain.

WORKING EXAMPLES

The effectiveness of the present compositions and methods were compared to existing compositions and methods as follows.

Example 1

Sixteen (16) volunteer patients were randomly chosen by using a table of random numbers from the practice of Hodosh Dental Associates. Each volunteer met the following inclusion/exclusion criteria:

1.) They had professionally confirmed periodontal disease based on the Gingival Health Scale set forth below in Table 1.

2.) They did not have a history of an untoward reaction (local or systemic) to potassium nitrate, dimethylisosorbide, or the remaining ingredients in mouthrinse (see below).

3.) They agreed to use an assigned mouthrinse b.i.d., and to keep weekly check-up visits for five (5) consecutive weeks.

4.) They had not used a potassium nitrate containing dentifrice for 1 month, and they could continue to use their usual home care regime if they chose to do so.

TABLE 1

Based on these alterations from normal, a systematic examination of the gingivae can be used to objectively quantify and qualify a patient's gingival health. The signs and symptoms indicative of periodontal disease were used to establish each patient's gingival health status.

A Normal Gingivae exhibits 3 mms.sulci depths as measured at 6 points (m, d, f; m, d, l). Gingival contour, consistency, surface texture, and color are within normal range. Gingival position exhibits no apical shift (recession) of the gingivii.
B Gingivae is slightly reddened, inflamed, and enlarged with early untoward changes in consistency, texture, contour, and color. There is slight bleeding on instrumentation and slight deepening of the gingival sulci (4–5 mms.) and little or no apical gingival shift.
C Gingivae shows moderate inflammation and enlargement along with moderate changes in contour, consistency, and texture. The color of the gingivii is a darker red and there is increased bleeding with instrumentation. There is moderate deepening of the gingival sulci (4–6 mm.), and there may be apical gingival shifting.

TABLE 1-continued

Based on these alterations from normal, a systematic examination of the gingivae can be used to objectively quantify and qualify a patient's gingival health. The signs and symptoms indicative of periodontal disease were used to establish each patient's gingival health status.

D  Gingivae is a darker bluish-red, enlarged, and tender with brushing, bleeds easily with instrumentation, and pocketing is encountered with a periodontal probe (6–8 mm.). Contour is not sharp interproximally nor knifelike; the consistency is boggy, and spongy, the texture is shiny, and smooth with a loss of stippling. Gingival apical shift may be present and can be measured.
E  Gingivae is dark red or dark reddish-purple, tender, and bleeds very easily with instrumentation, very enlarged(enlarged papillae also), and with very poor contour, consistency, and texture. Periodontal pockets ranged from 6–10+ mm. with the presence of apical gingival shifting. The gingivae may exhibit purulent or serous exudation.

Gingival health grading was used at weekly patient check-ups. Grading according to the Gingival Health Scale served as a means of assessing the effectiveness of the treatment used.

The aim of the study was to see if a mouthrinse containing dimethylisosorbide and saturated with potassium nitrate could physiologically inactivate and effectively eliminate the offending bacteria in the gingivo-dental anatomy and reverse their deleterious effects on the gingivii, connective tissue, junctional epithelium and underlying periodontium.

A mouthrinse (No. 1, No. 2, or No. 3) was assigned to and supplied to each patient in a 4 ounce flip top bottle.

Mouth rinse No. 1 contained about 35% KNO₃, about 10% DMI, and about 50% water plus flavoring.

Mouth rinse No. 2 contained about 35% KNO₃ and about 64% water plus flavoring.

Mouth rinse No. 3 contained water and flavoring.

Each of mouth rinses No. 1, No. 2, and No. 3 appeared identical and neither the clinician nor the patient knew which one was being used. Envelopes were numbered 1–16 and a slip of paper indicating which mouthrinse was assigned to each patient was inserted into each envelope. A master sheet describing the composition of each mouth rinse was placed in a locked drawer to be opened when the study was completed. Another sheet listed the patients serially by number (1–16). This sheet guided clinicians as to which mouthrinse was designated for each patient as they appeared in the study.

Each patient was examined clinically, given an initial gingival health grade and provided with a regimen for using the mouthwash. The instructions were to swish their designated mouthrinse about their gums and teeth for about 1–2 minutes and then expectorate. When they returned weekly, they were examined clinically and given a current gingival health grade. Photographs and x-rays were taken to illustrate progress or lack of it.

At the end of 5 weeks, the key was broken and the data collected and evaluated. All patients using the present mouthwash b.i.d. for 5 weeks had their gingivii return to normalcy and gingival health restored.

The gingivii has been found to be very resilient exhibiting a strong capability to return to normalcy when the putative bacteria for causing periodontal disease, their toxins, and gingival inflammatory components have been effectively eliminated. The results of Mouth Rinse No. 3 showed no change. The foregoing Mouth Rinse No. 1, used b.i.d. predictably and routinely cause the gingival contour, consistency, surface texture, and color to return to normal with notable periodontal pocket depth, bleeding, and gingival enlargement reduction. Gingival health was restored, even without the use of conventional treatment modalities such as deep scaling and curettage, apically positioned flaps, gingivectomy, gingivoplasty, papillectomy, or other methodologies. The results of Mouth Rinse No. 2 showed the same type of improvement as Mouth Rinse No. 1, but to a lesser degree.

When used on a regular basis, the putative bacteria may be depolarized and lysed by the compositions, eliminating the source of toxic emissions. Bacterial toxins and destructive enzymes that had penetrated into the periodontal ligament and alveolar bone were phagocytized by the immune system cells and carried away by the lymphatics allowing gingivial and other periodontal tissues to improve. Favorable conditions were created that allowed the reparative phase of periodontal disease to work positively for the deeper periodontal structures (connective tissues, bone, etc.).

By the same method of bacterial plaque destruction, those bacteria thought to cause dental caries (e.g. *streptococcus viridans*) are also effectively destroyed. In this way, potassium and DMI are effective caries fighter. They are the first caries fighters that appear effective since the discovery of fluoride. It is effective for regular caries prevention, as well as root caries prevention.

Example 2

Root caries is a significant dental problem, especially as one grows older and the dentin is exposed. In office cases, the present compositions and methods have proved to effectively prevent root caries especially in people with extensive fixed bridgework.

The foregoing compositions were applied to the gingiva/ dental complex (the gums and teeth) and effectively eliminated the calculus/(bacterial) plaque attached to the teeth. This lead to the gingival inflammation subsiding and to the deeper periodontal tissues (junctional epithelium, connecting tissue and bone) becoming healthier.

Gingival bleeding, color, consistency, contour, texture, and periodontal pockets routinely became more normal (usually normal).

Thus, the present compositions and methods were effective for preventing periodontal disease and for restoring the gingivae to health. This will result in improvement to the deeper periodontal tissues to better health and promote repair of the same.

Example 3

When the mouthrinse #1 were applied immediately prior to undergoing scaling procedures in the office (Hygienist/ dentist), the plaque/calculus complex attached to the teeth softened and appeared to swell considerably and the firmness of its attachment to the teeth lessened. Removal of the calculus with hand or mechanical, or ultrasound sealers became extremely easy to remove, and the teeth's roots were left unusually smooth and clean. The dental plaque/calculus deposits were easier to remove. Without the mouthrinse application, the calculus deposits normally would adhere very tenaciously to the teeth, especially subgingivally.

Therefore, the present compositions provide an effective pre-scaling substance which makes calculus removal easier, and of course, the patient more comfortable when undergoing this procedure (deep scaling and curetage).

Example 4

The literature attests to the major role played by the microbiota in causing periodontal disease mouth odor, and caries in man. Destruction of the sulfur producing bacteria located in plaque, which causes most mal mouth odor, prevents the sulfur compounds from getting into the patients' tongue. Therefore, the present compositions and methods may be effective in fighting bad breath (fetor ex or—also known as halitosis).

Although particular embodiments of the disclosure have been described in detail for purposes of illustration, various changes and modifications may be made without departing from the scope and spirit of the disclosure. All combinations and permutations of the compositions and methods are available for practice in various applications as the need arises. For example, bacteria producing skin disease may be destroyed as described above when the present compositions are applied topically to the derma or skin. applied to processes that are presently not practically feasible. Accordingly, the disclosure is not to be limited except as by the appended claims.

The invention claimed is:

1. A method for inhibiting the formation of plaque of the gingivo-dental anatomy in a subject, the method comprising the step of:
    periodically applying an effective amount of a composition containing potassium as an ingredient to a region of the gingivo-dental anatomy of the subject, and an osmotic agent, the concentration of the potassium containing compound of at least 10 weight percent up to the saturation level of the potassium containing compound, wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

2. The method of claim 1, wherein the osmotic agent is dimethyl isosorbide.

3. The method of claim 1, wherein the method further inhibits the formation of calculus in the subject.

4. The method of claim 1, wherein the method further inhibits gingival disease.

5. The method of claim 1, wherein the method further inhibits periodontal disease.

6. The method of claim 1, wherein the method inhibits CAD.

7. A method for inhibiting periodontal disease, comprising:
    applying an effective amount of a mouthwash to a region of the gingivo-dental anatomy of a subject, the mouthwash containing a concentration of a potassium containing compound and containing an osmotic agent, such that the potassium inhibits the formation of plaque-forming bacteria in the gingivo-dental anatomy, the concentration of the potassium containing compound of at least 10 weight percent up to the saturation level of the potassium containing compound wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylbutylisosorbide, ethylpropylisosorbide and ethylbutylisosorbide, and combinations thereof.

8. The method of claim 1, wherein the composition contains potassium from a potassium containing compound selected from the group consisting of potassium bicarbonate, potassium biphthalate, potassium bromide, potassium chromate, potassium acetate, potassium dichromate, potassium phosphate, potassium sulfate, potassium chromium sulfate, potassium citrate, potassium thiocyanate, potassium alum, potassium bitartrate, potassium bromate, potassium carbonate, potassium chlorate, potassium chloroglatinate, potassium chloride, potassium hydroxide, potassium perchlorate, potassium persulfate, potassium oxalate, potassium azide, potassium fluoride, potassium hydrogen sulfate, potassium iodate, potassium sodium wherein the composition contains potassium from potassium nitrate, tartrate, potassium fluoride, tartrate, and combinations thereof.

9. The method of claim 1, wherein the composition contains potassium from potassium nitrate.

10. The method of claim 1 wherein the concentration of the potassium containing compound is at least 20 weight percent.

11. The method of claim 7 wherein the concentration of the potassium containing compound is at least 20 weight percent.

12. The method of claim 1, wherein the potassium containing compound comprises an anti-inflammatory agent.

13. The method of claim 1, wherein the potassium containing compound comprises an anti-bacterial agent.

14. The method of claim 7, wherein the potassium containing compound comprises an anti-inflammatory agent.

15. The method of claim 7, wherein the potassium containing compound comprises an anti-bacterial agent.

16. The method of claim 1, wherein the concentration of potassium containing compound is in a range of 10–20 weight percent.

17. The method of claim 7, wherein the concentration of potassium containing compound is in a range of 10–20 weight percent.

18. The method of claim 1, wherein the potassium containing compound is an essential ingredient.

19. A method for inhibiting the formation of plaque of the gingivo-dental anatomy in a subject, the method comprising the step of:
    periodically applying an effective amount of a composition containing potassium as an ingredient to a region of the gingivo-dental anatomy of the subject, and an osmotic agent, the concentration of the potassium containing compound is in a range of 10–20 weight percent wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

20. The method of claim 19 wherein the osmotic agent is dimethyl isosorbide.

21. The method of claim 19 wherein the composition contains potassium from potassium nitrate.

22. A method for inhibiting periodontal disease, comprising:
    applying an effective amount of a mouthwash to a region of the gingivo-dental anatomy of a subject, the mouthwash containing a concentration of a potassium containing compound and containing an osmotic agent, such that the potassium inhibits the formation of plaque-forming bacteria in the gingivo-dental anatomy, the concentration of the potassium containing compound is in a range of 10–20 weight percent wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

23. The method of claim 22 wherein the osmotic agent is dimethyl isosorbide.

24. The method of claim 22 wherein the composition contains potassium from potassium nitrate.

25. A method for inhibiting the formation of plaque of the gingivo-dental anatomy in a subject, the method comprising the step of:
periodically applying an effective amount of a composition containing potassium as an ingredient to a region of the gingivo-dental anatomy of the subject, and an osmotic agent, wherein the composition contains potassium from potassium nitrate, and the concentration of the potassium containing compound is about 35 weight percent wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

26. The method of claim 25 wherein the osmotic agent is dimethyl isosorbide.

27. A method for inhibiting periodontal disease, comprising:
applying an effective amount of a mouthwash to a region of the gingivo-dental anatomy of a subject, the mouthwash containing a concentration of a potassium containing compound and containing an osmotic agent, such that the potassium inhibits the formation of plaque-forming bacteria in the gingivo-dental anatomy, wherein the composition contains potassium from potassium nitrate, and the concentration of the potassium containing compound is about 35 weight percent wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

28. The method of claim 27 wherein the osmotic agent is dimethyl isosorbide.

29. A method for inhibiting the formation of plaque of the gingivo-dental anatomy in a subject, the method comprising the step of:
periodically applying an effective amount of a composition containing potassium as an ingredient to a region of the gingivo-dental anatomy of the subject, and an osmotic agent, wherein the composition contains potassium from potassium nitrate, and the concentration of the potassium containing compound is in a range from about 3 weight percent up to the saturation level of the potassium containing compound wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

30. The method of claim 29 wherein the concentration of the potassium containing compound is at least 10 weight percent.

31. The method of claim 29 wherein the concentration of the potassium containing compound is at least 20 weight percent.

32. The method of claim 29, wherein the concentration of potassium containing compound is in a range of 10–20 weight percent.

33. The method of claim 29 wherein the osmotic agent is dimethyl isosorbide.

34. A method for inhibiting periodontal disease, comprising:
applying an effective amount of a mouthwash to a region of the gingivo-dental anatomy of a subject, the mouthwash containing a concentration of a potassium containing compound and containing an osmotic agent, such that the potassium inhibits the formation of plaque-forming bacteria in the gingivo-dental anatomy, wherein the composition contains potassium from potassium nitrate, and the concentration of the potassium containing compound is in a range from about 3 weight percent up to the saturation level of the potassium containing compound wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

35. The method of claim 34 wherein the concentration of the potassium containing compound is at least 10 weight percent.

36. The method of claim 34 wherein the concentration of the potassium containing compound is at least 20 weight percent.

37. The method of claim 34, wherein the concentration of potassium containing compound is in a range of 10–20 weight percent.

38. The method of claim 34 wherein the osmotic agent is dimethyl isosorbide.

39. A method for inhibiting the formation of plaque of the gingivo dental anatomy in a subject, the method comprising the step of:
periodically applying an effective amount of a composition containing potassium as an ingredient to a region of the gingivo-dental anatomy of the subject, and an osmotic agent, wherein the concentration of the potassium containing compound is at least about 3 weight percent and wherein the potassium containing compound is selected from the group consisting of potassium phosphate, potassium nitrate, potassium bicarbonate, potassium biphthalate, potassium chromate, potassium acetate, potassium dichromate, potassium chromium sulfate, potassium citrate, potassium thiocyanate, potassium alum, potassium bitartrate, potassium bromate, potassium carbonate, potassium chlorate, potassium chloroglatinate, potassium hydroxide, potassium perchlorate, potassium persulfate, potassium oxalate, potassium azide, potassium hydrogen sulfate, potassium iodate, potassium sodium tartrate and combinations thereof wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

40. The method of claim 39 wherein the potassium containing compound is at least about 10 weight percent.

41. The method of claim 39 wherein the potassium containing compound is at least about 20 weight percent.

42. A method for inhibiting periodontal disease, comprising:

applying an effective amount of a mouthwash to a region of the gingivo-dental anatomy of a subject, the mouthwash containing a concentration of a potassium containing compound and containing an osmotic agent, such that the potassium inhibits the formation of plaque-forming bacteria in the gingivo-dental anatomy, wherein the concentration of the potassium containing compound is at least about 3 weight percent and wherein the potassium containing compound is selected from the group consisting of potassium phosphate, potassium nitrate, potassium bicarbonate, potassium biphthalate, potassium chromate, potassium acetate, potassium dichromate, potassium chromium sulfate, potassium citrate, potassium thiocyanate, potassium alum, potassium bitartrate, potassium bromate, potassium carbonate, potassium chlorate, potassium chloroglatinate, potassium hydroxide, potassium perchlorate, potassium persulfate, potassium oxalate, potassium azide, potassium hydrogen sulfate, potassium iodate, potassium sodium tartrate and combinations thereof wherein the osmotic agent is selected from the group consisting of methylisosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide, and combinations thereof.

43. The method of claim 42 wherein the potassium containing compound is at least about 10 weight percent.

44. The method of claim 42 wherein the potassium containing compound is at least about 20 weight percent.

* * * * *